United States Patent
Hauck

(10) Patent No.: US 7,885,707 B2
(45) Date of Patent: Feb. 8, 2011

(54) METHOD OF SCALING NAVIGATION SIGNALS TO ACCOUNT FOR IMPEDANCE DRIFT IN TISSUE

(75) Inventor: John A. Hauck, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1243 days.

(21) Appl. No.: 11/227,580

(22) Filed: Sep. 15, 2005

(65) Prior Publication Data

US 2007/0060833 A1   Mar. 15, 2007

(51) Int. Cl.
*A61B 5/05* (2006.01)
(52) U.S. Cl. ...................................... 600/547
(58) Field of Classification Search ............... 600/544, 600/545, 547, 500, 503, 409, 508
See application file for complete search history.

(56) References Cited

U.S. PATENT DOCUMENTS

| | | | |
|---|---|---|---|
| 4,901,725 A * | 2/1990 | Nappholz et al. ............ 607/17 |
| 4,940,064 A | 7/1990 | Desai |
| 5,027,813 A | 7/1991 | Pederson et al. |
| 5,074,303 A | 12/1991 | Hauck et al. |
| 5,215,103 A | 6/1993 | Desai |
| 5,231,995 A | 8/1993 | Desai |
| 5,280,429 A | 1/1994 | Withers |
| 5,284,136 A | 2/1994 | Hauck et al. |
| 5,318,597 A | 6/1994 | Hauck et al. |
| 5,335,668 A | 8/1994 | Nardella |
| 5,397,339 A | 3/1995 | Desai |
| 5,500,011 A | 3/1996 | Desai |
| 5,511,553 A * | 4/1996 | Segalowitz ................. 600/508 |
| 5,553,611 A | 9/1996 | Budd et al. |
| 5,568,809 A | 10/1996 | Ben-haim |
| 5,697,377 A | 12/1997 | Wittkampf |
| 5,713,946 A | 2/1998 | Ben-Haim |
| 5,732,710 A | 3/1998 | Rabinovich et al. |
| 5,876,336 A | 3/1999 | Swanson et al. |
| 5,941,251 A | 8/1999 | Panescu et al. |
| 5,983,126 A | 11/1999 | Wittkampf |
| 6,070,094 A | 5/2000 | Swanson et al. |
| 6,095,150 A | 8/2000 | Panescu et al. |
| 6,353,751 B1 | 3/2002 | Swanson et al. |
| 6,456,864 B1 | 9/2002 | Swanson et al. |
| 6,516,807 B1 | 2/2003 | Panescu et al. |

(Continued)

OTHER PUBLICATIONS

International Search Report, Aug. 17, 2007, and Written Opinion of the International Searching Authority for PCT/US2006/035585, Aug. 17, 2007.

(Continued)

*Primary Examiner*—Max Hindenburg
*Assistant Examiner*—Fangemonique Smith
(74) *Attorney, Agent, or Firm*—Heimbecher & Assoc., LLC

(57) ABSTRACT

A method for scaling the impedance measured during the course of an electrophysiology study accounts for impedance drifts. By scaling the impedance there is greater assurance that previously recorded positional information can be used to accurately relocate an electrode at a prior visited position. The scale factor may be based upon a mean value across several sensing electrodes. Alternatively, the scale factor may be calculated specifically with respect to an orientation of a dipole pair of driven electrodes.

17 Claims, 4 Drawing Sheets

U.S. PATENT DOCUMENTS

| | | |
|---|---|---|
| 6,600,948 B2 | 7/2003 | Ben-Haim et al. |
| 6,681,131 B2 * | 1/2004 | Kandori et al. ............. 600/409 |
| 6,728,562 B1 | 4/2004 | Budd et al. |
| 6,730,038 B2 * | 5/2004 | Gallant et al. ............... 600/485 |
| 7,187,968 B2 * | 3/2007 | Wolf et al. .................. 600/544 |
| 2004/0254437 A1 | 12/2004 | Hauck et al. |
| 2005/0203394 A1 | 9/2005 | Hauck |

OTHER PUBLICATIONS

Extended European Search Report for European Application No. EP 06814553.1 dated Jun. 4, 2009.

* cited by examiner

| Dipole (ImpNum) | Left Patch (Xa) | Right Patch (Xb) | Back Patch (Ya) | Chest Patch (Yb) | Neck Patch (Za) | Left Leg Patch (Zb) |
|---|---|---|---|---|---|---|
| Xa–Ya (0) |  | X |  |  | X |  |
| Xa–Yb (1) |  | X |  |  | X |  |
| Xb–Ya (2) | X |  |  | X |  |  |
| Xb–Yb (3) | X |  | X |  | X |  |
| Za–Ya (4) | X | X |  |  |  |  |
| Zb–Ya (5) |  |  |  | X |  |  |

Fig. 3

METHOD OF SCALING NAVIGATION SIGNALS TO ACCOUNT FOR IMPEDANCE DRIFT IN TISSUE

BACKGROUND OF THE INVENTION

1. Field of the Invention

This invention relates to systems for positioning and mapping electrophysiology catheters and ablation catheters in the heart of a patient. The invention further relates to methods for error correction in electrocardiograph signals.

2. Background Art

U.S. Pat. Nos. 5,697,377 (the '377 patent) and 5,983,126 (the '126 patent) to Wittkampf disclose a system for determining the position or location of a catheter in the heart. The '377 patent and the '126 patent are hereby incorporated herein by reference in their entirety. In the Wittkampf system, current pulses are applied to orthogonally placed patch electrodes placed on the surface of the patient. These surface electrodes are used to create axis specific electric fields within the patient. The Wittkampf references teach the delivery of small amplitude, low current pulses supplied continuously at three different frequencies, one on each axis. Any measurement electrode placed in these electric fields (for example within the heart) measures a voltage that varies depending on the location of the measurement electrode between the various surface electrodes on each axis. The voltage across the measurement electrode in the electric field in reference to a stable positional reference electrode indicates the position of the measurement electrode in the heart with respect to that reference. Measurement of the difference in voltage over the three separate axes gives rise to positional information for the measurement electrode in three dimensions.

Although the Wittkampf system is both safe and effective there are several factors that can result in errors in the position of the measurement electrode. Some factors previously identified as sources of impedance modulation include the cardiac cycle and respiration. Both of these sources also cause actual physical movement of an electrode in addition to direct impedance effects. Mitigations to these modulators to enhance stability of electrode positional measurements include low pass filtering, cardiac cycle triggering, and respiration compensation. One factor not previously addressed is the tendency of biologic impedance to change over time. Changes in biologic impedance are attributable to changes in cell chemistry, for example, due to saline or other hydration drips in the patient, dehydration, or changes in body temperature.

If the biologic impedance changes over a longer term (i.e., minutes or hours), then apparent shifts of the measured locations of electrodes may occur. If an internal cardiac electrode is used as a reference electrode, these shifts may be negligible, since they are manifest as a scale factor change of only a few percent. For example, a 2 percent change with respect to a fixed reference 4.0 centimeters away will represent an error of 0.8 millimeters, which is generally considered acceptable. However, if it is desired to use an external body surface electrode as a fixed reference, and eliminate the requirement of a fixed intra-cardiac electrode reference, then 2 percent may represent an intolerable error source. For example, if the reference electrode is an "apparent" 40 cm from a mapping electrode, the error due to a 2% impedance drift would be 8 millimeters. The term "apparent" is used because while the actual distance to the reference electrode may be somewhat less, the intervening biologic of lung and muscle tissue is higher than that of blood, such that it scales to a larger distance.

The information included in this Background section of the specification, including any references cited herein and any description or discussion thereof, is included for technical reference purposes only and is not to be regarded subject matter by which the scope of the invention is to be bound.

SUMMARY OF THE INVENTION

The present invention addresses the problem of biologic impedance changes and the effect on measurement of the position of an electrode within a patient by continuously calculating a scale factor to apply to impedance measurements throughout the course of a procedure. Changes in biologic impedance attributable to changes in cell chemistry, for example, due to saline or other hydration drips in the patient, dehydration, or changes in body temperature, can thus be accounted for and a more accurate positional reading for a measurement electrode may be obtained.

In one form, the invention may be understood as a method for scaling impedance measurements in an electrophysiology study. A first dipole is driven along a first axis to create an electric field across a patient's body. A biologic impedance encountered by the electric field with respect to a surface sensor is measured. The mean of the absolute value of the measured biologic impedance is calculated continuously as a function of time Pm(t). An initial calculated mean of the absolute value of the at least one measured biologic impedance is saved as Pa. An impedance measurement between a measurement electrode and a reference electrode is then multiplied by the ratio of Pa/Pm(t) to scale the impedance measurement and account for any drift. This scaling calculation may be performed by software controlling an electrophysiology study or ablation system. The invention may further break the scale factors into component scales with respect to a plurality of dipole axes that may be driven. In this instance, separate measurements for each axis are measured and the scale factor is represented by Pa(i)/Pm(t,i), where (i) indicates the axis of measurement.

Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIG. 3 is a table indicating the surface electrodes used as sensors when a particular dipole pair of surface electrodes is driven.

DETAILED DESCRIPTION OF THE INVENTION

One of the primary goals of cardiac electrophysiology mapping is to locate with some certainty the position of an electrode within a cardiac cavity. An electric navigation field is created within a patient's body on each of the three principal axes by driving a constant current. If the impedances measured in the body are constant, then the potentials on each axis measured at a location, with respect to a reference electrode at a static location, will remain at a constant potential over time. Thus, if a location site is marked in the heart, one may return to that site with a catheter electrode in the future and be confident that if the measured navigation potentials, or impedance, are the same as before, the anatomic location is the same.

Figure 1:
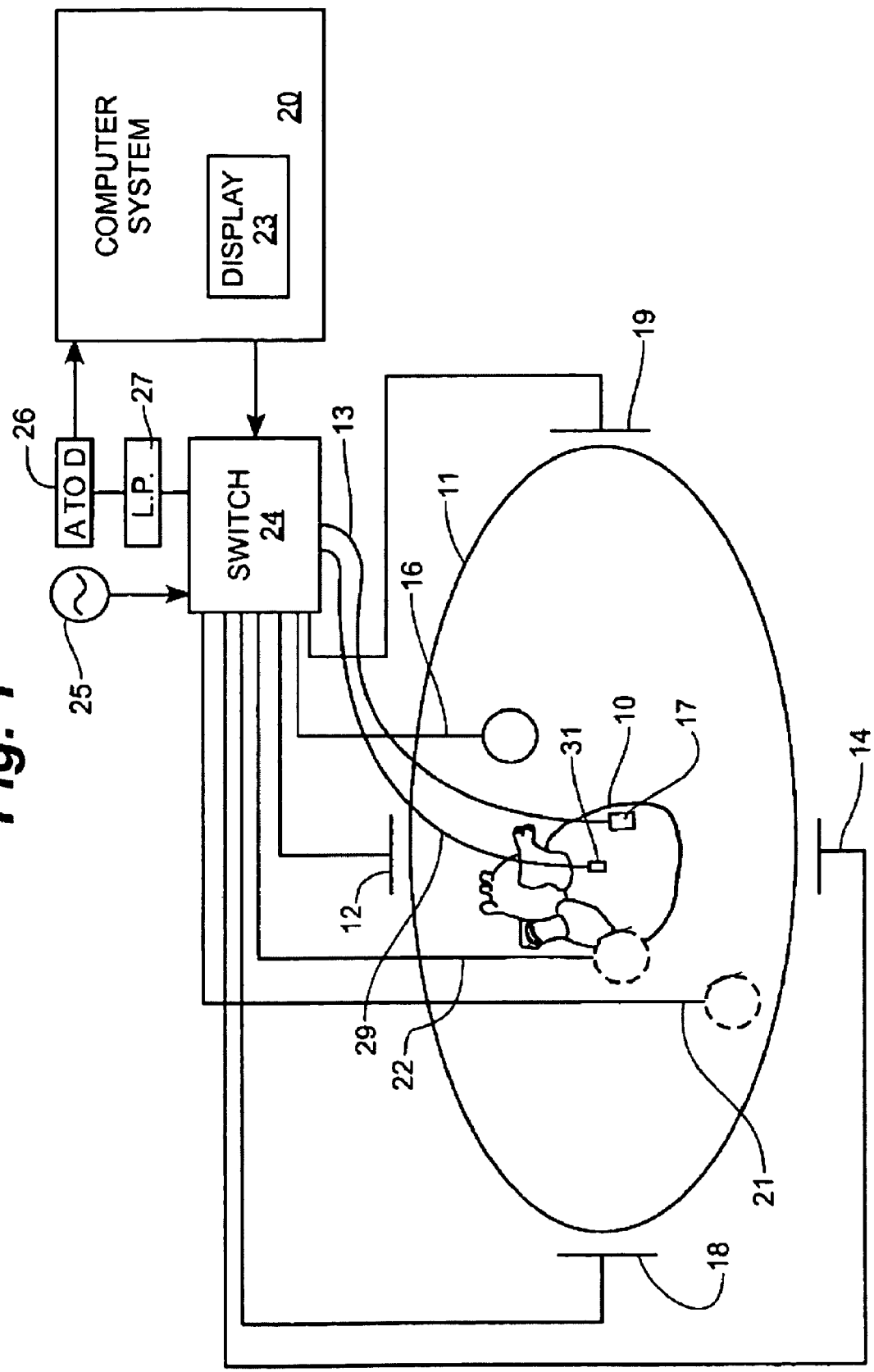
FIG. 1 is a schematic diagram of a system for performing a cardiac electrophysiology examination or ablation procedure wherein the location of one or more electrodes can be determined and recorded.

FIG. 1 depicts a schematic diagram of an exemplary electrophysiology mapping or ablation system. The patient 11 is depicted as an oval for clarity. Three sets of surface electrodes (e.g., patch electrodes) are shown applied to a surface of the patient 11 along an X-axis, a Y-axis, and a Z-axis. The X-axis surface electrodes 12, 14 are applied to the patient along a first axis, such as on the lateral sides of the thorax region of the patient (e.g., applied to the patient's skin underneath each arm) and may be referred to as the Left and Right electrodes. The Y-axis electrodes 18, 19 are applied to the patient along a second axis generally orthogonal to the X-axis, such as along the sternum and spine of the patient in the thorax region and may be referred to as the Chest and Back electrodes. The Z-axis electrodes 16, 22 are applied along a third axis generally orthogonal to both the X-axis and the Y-axis, such as along the:inner thigh and neck regions of the patient, and may be referred to as the Left Leg and Neck electrodes. The heart 10 lies between these pairs of surface electrodes. An additional surface reference electrode (e.g., a "belly patch") 21 provides a reference and/or ground electrode for the system 8. The belly patch electrode 21 is an alternative to a fixed intracardiac electrode 31. It should also be appreciated that in addition, the patient 11 will have most or all of the conventional electrocardiogram (ECG) system leads in place. This ECG information is available to the system although not illustrated in the FIG. 1.

A representative catheter 13 with a single, distal measurement electrode 17 is also depicted in FIG. 1. The catheter 13 may also have additional electrodes in addition to the measurement electrode 17. A fixed reference electrode 31 may be attached to a heart wall on an independent catheter 29. In many instances, a coronary sinus electrode or other fixed reference electrode 31 in the heart 10 can be used as a reference for measuring voltages and displacements. For calibration purposes the reference electrode 31 remains stationary on the wall of the heart during the course of the procedure.

Each surface electrode is independently connected to a multiplex switch 24. Pairs of the surface electrodes are selected by software running on a computer 20, which couples the surface electrodes 12, 14, 16, 18, 19, 21, 22 to a signal generator 25. A first pair of surface electrodes, for example, the Z-axis electrodes 18, 19, is excited by the signal generator 25. The exited electrodes generate an electric field in the body of the patient 11 and the heart 10. This electrode excitation process occurs rapidly and sequentially as alternate sets of patch electrodes are selected and one or more of the unexcited surface electrodes are used to measure voltages. During the delivery of a current pulse, the unexcited surface electrodes 12, 14, 16, and 22 are referenced to either the reference electrode 31 or the belly patch 21 and respective voltages are measured across one or more of these unexcited electrodes. In this way, the surface electrodes are divided into driven and non-driven electrode sets.

While a pair of electrodes is driven by the current generator 25, the remaining, non-driven electrodes may be used as references to synthesize the orthogonal drive axes. A low pass filter 27 processes the voltage measurements to remove electronic noise and cardiac motion artifact from the measurement signals. The filtered voltage measurements are transformed to digital data by the analog to digital converter 26 and transmitted to the computer 20 for storage under the direction of software. This collection of voltage measurements is referred to herein as the "patch data." The software has access to each individual voltage measurement made at each surface electrode during each excitation of each pair of surface electrodes. The patch data is used to determine a relative location in three dimensions (X, Y, Z) of the measurement electrode 17. Potentials across each of the six orthogonal surface electrodes may be acquired for all samples except when a particular surface electrode pair is driven. Sampling while a surface electrode acts as a source or sink in a driven pair is normally avoided as the potential measured at a driven electrode during this time will be skewed by the electrode impedance and the effects of high local current density.

Generally, three nominally orthogonal electric fields are generated by a series of driven and sensed electric dipoles in order to realize catheter navigation in a biological conductor. Alternately, these orthogonal fields can be decomposed and any pairs of surface electrodes can be driven as dipoles to provide effective electrode triangulation. Additionally, such nonorthogonal methodologies add to the flexibility of the system and the ability to localize biologic impedance compensation. For any desired axis, the potentials measured across an intra-cardiac electrode 17 resulting from a predetermined set of drive (source-sink) configurations are combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, e.g., the belly patch 21, while the unexcited electrodes measure voltage with respect to the ground reference. The measurement electrode 17 placed in the heart 10 is exposed to the field from a current pulse and is measured with respect to ground, e.g., the belly patch 21. In practice the catheters within the heart may contain multiple electrodes and each electrode potential may be measured. As previously noted, at least one electrode may be fixed to the interior surface of the heart to form a fixed reference electrode 31, which is also measured with respect to ground. Data sets from each of the surface electrodes and the internal electrodes are all used to determine the location of the measurement electrode 17 within the heart 10. After the voltage measurements are made, a different pair of surface electrodes is excited by the current source and the voltage measurement process of the remaining patch electrodes and internal electrodes takes place. The sequence occurs rapidly on the order of 100 times per second. To a first approximation the voltage on the electrodes within the heart bears a linear relationship with position between the patch electrodes that establish the field within the heart. Correction factors, e.g., to compensate for respiration, may be applied to the raw location information to improve the accuracy of the location value.

Figure 4:
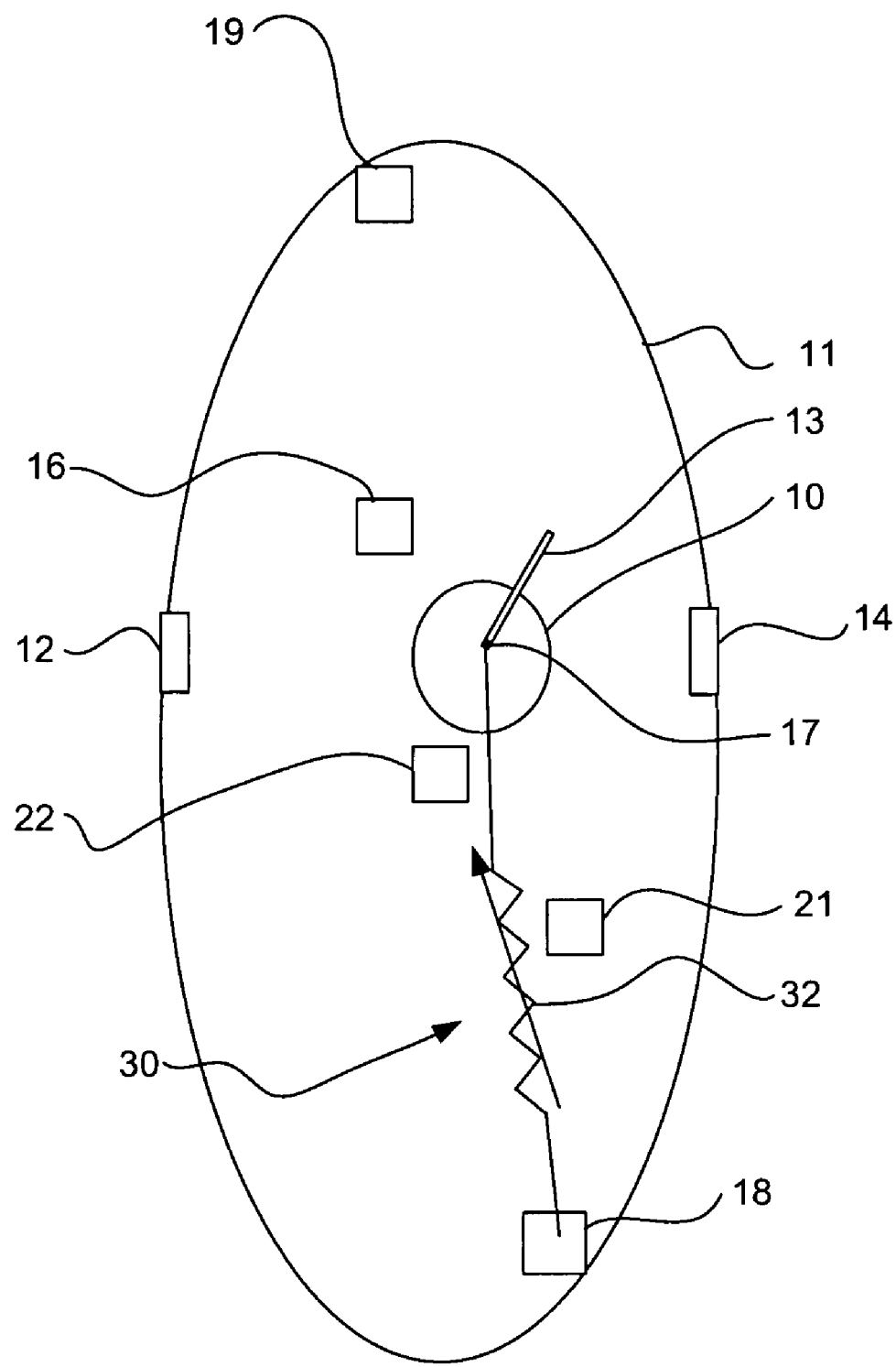
FIG. 4 is a schematic diagram of biologic impedance drift portrayed as an electrical circuit.

When operating with constant currents during an electrophysiology study, the potentials created with respect to any reference will be a function of the intervening impedance. This concept is represented schematically in FIG. 4. A catheter 13 with a distal measurement electrode 17 is placed within the heart 10 of the patient 11. A set of orthogonal surface electrodes 12, 14, 16, 18, 19, 22 are alternately paired as drive electrodes while the remaining, unexcited electrodes may function as sensor electrodes. The electric potential generated by a dipole pair of electrodes may be measured at a measurement electrode in the body and the path of current through the body between the driven surface electrode and the distal measurement electrode 17 on the catheter may be understood simply as a circuit. For example, as shown in FIG. 4, when the Left Leg electrode 18 is driven as a source, a circuit 30 is created between the Left Leg electrode 18 and the measurement electrode 17 on the catheter 13 within the heart 10. The body tissue between the skin at the Left Leg electrode 12 and the heart 10 acts primarily as a resistive impedance and can be viewed functionally as a resistor 32. However, due to changes in body chemistry during a procedure, the value of this resistor 32 may drift. Therefore, the resistor 32 may be more accurately viewed as a variable resistor as depicted. It should be apparent that if the tissue impedance changes, then the voltage data and thus positional data for each electrode, including a reference electrode, e.g., the belly patch electrode 21, will similarly drift.

To the extent that intervening impedances change after a study begins and sites have been marked, attempts to place the measurement electrode at previously visited locations may not be consistent with earlier marked sites. To the extent that the impedance change for a given pair of drive surface electrode dipoles is tracked by unexcited surface electrodes used as sensors, these data may be used to correct the drift on each driven dipole. This is best done by using the surface electrode patches as sensors in the time slices when they are un-driven. Two exemplary methods are discussed herein to account for and correct any potential drift. The first method assumes that the bio-impedance changes are essentially homogeneous. Thus all driven dipoles change by the same percentage and averaging of all the patch data returns a single impedance index. The second method does not make this assumption and computes an index for each axis.

A first method for biologic impedance scaling assumes that any biologic impedance changes are essentially homogenous within the body, that all dipoles change by the same percentage, and that averaging of all surface electrode data will provide a single, accurate impedance index. The method uses the Neck, Left, Right, Chest, and Back surface electrode patches as sensors when they are not being driven. The Left Leg electrode is not generally used for sensing because sensed potentials on it tend to be very small. For pairings of the driven surface electrode excluding the Left Leg, there are thus three potential sense patches that contribute data. In the case of driven pairings including the Left Leg, four surface electrode patches are available as sensors. The mean of the absolute values of the measured impedance at the surface electrode sensors is obtained continuously as a function of time. This mean value may be denoted as $Pm(t)$. Immediately after the a study begins, the initial value of $Pm(t)$ is saved as an initial value Pa. On every subsequent sample, all of the measurement electrode data is multiplied by the ratio $Pa/Pm(t)$. The three dimensional impedance measurements are thereby scaled to account for any drift over time.

To illustrate, a study begins and, assuming there are no errors due to unconnected surface electrodes, the surface electrodes are each sensed during their un-driven phases and averaged to yield a Pa of 10.0 ohms, which is saved in the software on the computer 20. Assume an important site is marked with a measurement electrode on a catheter in the heart at a site with the impedance coordinates of (1.0, 2.0, 10.0) ohms with respect to a belly patch reference electrode 21. These impedance coordinates are translated for the user using a nominal scale factor to yield positional coordinates of (25, 50, 400) millimeters. Suppose, due to a saline drip or other factors, an hour later the patient's biologic impedance has lowered by 2%. Without compensation, a return visit by a catheter electrode to the marked anatomic site would now show up at coordinates of (24.5, 49.0, 392.0) millimeters, a drift of 8 millimeters. However, the same biologic impedance drift will be registered on the data sensed by the surface electrodes. For example, $Pm(t)$ will now read 9.8 ohms. Therefore, scaling the catheter electrode coordinate data by $Pa/Pm(t)$, or 1.0204, will ensure the catheter electrode is positioned at its original and correct location.

A second method for scaling biologic impedance shifts according to the present invention is generally the same as in the prior embodiment, except that separate scale factors are maintained for each axis or pair of driven electrode dipoles. While it is generally found that biologic impedance drifts are essentially homogeneous, this method may be preferred in the event that biologic impedance drifts are not homogeneous throughout the measurement space. In this instance a value, $Pm(i,t)$, the mean of the absolute values of the measured impedance of each of the dipole combinations as a function of time, can be calculated. In this method, $Pm(i,t)$ for each dipole pair are computed, where "i" is the dipole number, or "Impedance Number," by averaging the impedance measurements at the surface electrodes on a dipole basis. Notably, not all of the undriven surface electrodes need be averaged to optimally determine the axial impedance for each dipole. Thus, the initial value of patch impedance, $Pa(i)$, and subsequent values of patch impedance, $Pa(i,t)$, may be measured for each dipole by averaging only the electrode data per the table of FIG. 3 for that dipole.

Figure 2A:
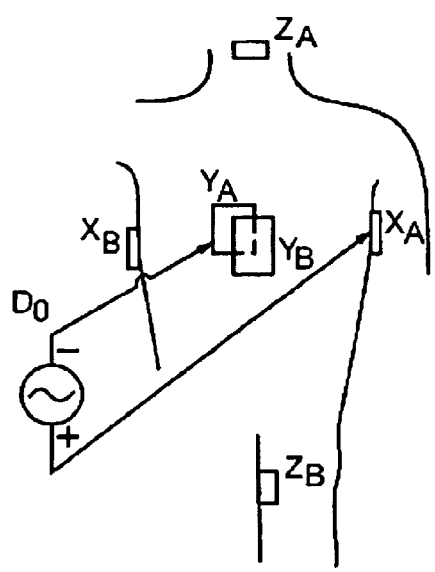
FIGS. 2A-2D are schematic diagrams of dipole pairs of driven surface electrodes.
Figure 2B:
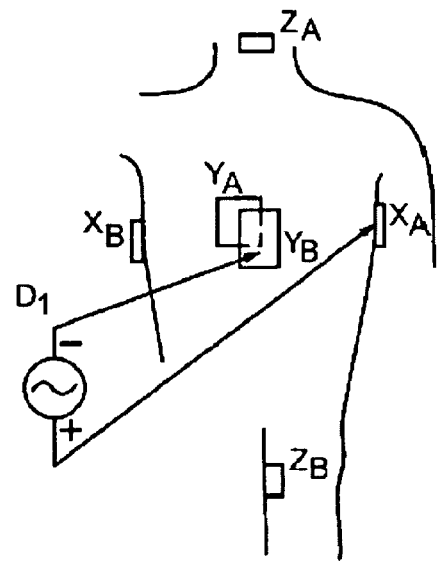
Figure 2C:
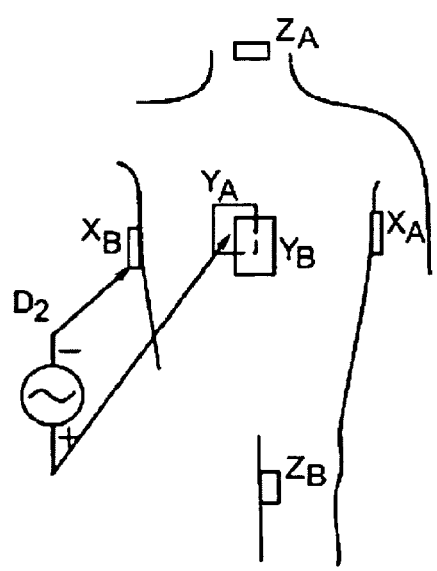
Figure 2D:
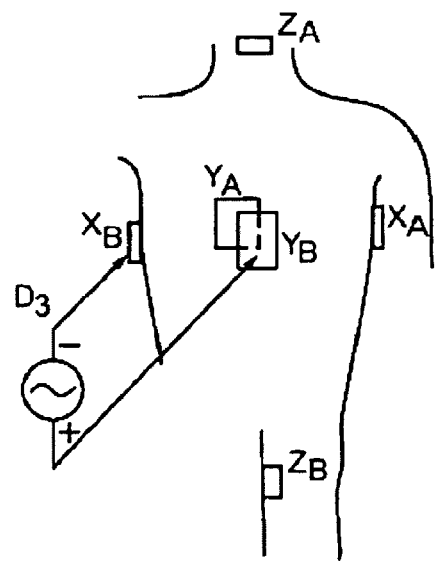

As shown in FIG. 3, the measured impedance for a first dipole Xa-Ya (0) between the Left electrode and the Back electrode may be obtained by averaging the Right electrode (Xb) and the Neck electrode (Za) data. This dipole is depicted in FIG. 2A. Similarly, the measured impedance for a second dipole Xa-Yb (1) between the Left electrode and the Chest electrode may also be obtained by averaging the Right electrode (Xb) and the Neck electrode (Za) data. This dipole is depicted in FIG. 2B. The measured impedance for a third dipole Xb-Ya (2) driven between the Right electrode and the Back electrode may be obtained by averaging the Left electrode (Xb) and the Chest electrode (Yb) data. This dipole is depicted in FIG. 2C. The measured impedance for a fourth dipole Xb-Yb (3) driven between the Right electrode and the Chest electrode may be obtained by averaging the Left electrode (Xb), the Back electrode (Ya) and the Neck electrode (Yb) data together. This dipole is depicted in FIG. 2D. The measured impedance for a fifth dipole Za-Ya (4) driven between the Neck electrode and the Back electrode may be obtained by averaging the Left electrode (Xa) and the Right electrode (Xb) data together. Finally, the measured impedance for a sixth dipole is Zb-Ya (5) driven between the left Leg electrode and the Back electrode may be optimally obtained by recoding date for the Chest electrode (Xa) only.

It should be noted that while biologic impedance scaling will have the greatest effect when correcting impedance changes when a body surface electrode is used as a reference electrode, such scaling may also be applied to cases where an intra-cardiac reference electrode is used. There is simply less error to correct for in the latter case.

Although various embodiments of this invention have been described above with a certain degree of particularity, or with reference to one or more individual embodiments, those skilled in the art could make numerous alterations to the disclosed embodiments without departing from the spirit or scope of this invention. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A method for scaling impedance measurements in an electrophysiology study, the method comprising
providing an electrophysiology system capable of generating an electric field across a patient's body;
driving a first dipole along a first axis to create an electric field across a patient's body;
measuring at least one biologic impedance encountered by the electric field with respect to at least one surface sensor;
calculating the mean of the absolute value of the at least one measured biologic impedance continuously as a function of time Pm(t);
saving an initial calculated mean of the absolute value of the at least one measured biologic impedance as Pa; and
multiplying an impedance measurement between a measurement electrode and a reference electrode by the ratio of Pa/Pm(t).

2. The method of claim 1, wherein
the at least one surface sensor comprises a plurality of surface sensors;
the step of calculating further comprises calculating the mean of the absolute values of the at least one measured biologic impedance as a function of time at each of the plurality of surface sensors; and
the step of saving further comprises saving the initial calculated mean of the absolute values of the of the measured biologic impedance at each of the plurality of surface sensors.

3. The method of claim 1, wherein
the step of driving further comprises driving a second dipole along a second axis across the patient's body;
the step of calculating further comprises calculating means of the absolute values of the measured biologic impedance as a function of time at the at least one surface sensor with respect to both the first dipole and the second dipole separately as Pm(t,i);
the step of saving further comprises saving an initial calculated mean of the absolute values of the measured biologic impedance for each of the first dipole and the second dipole separately as Pa(i); and
the step of multiplying further comprises multiplying an impedance measurement at the measurement electrode with respect to each of the first dipole and the second dipole by the respective ratio of Pa(i)/Pm(t,i).

4. The method of claim 3, wherein
the at least one surface sensor comprises a plurality of surface sensors;
the step of calculating further comprises calculating the mean of the absolute values of the measured biologic impedance as a function of time at each of the plurality of surface sensors; and
the step of saving further comprises saving the initial calculated mean of the absolute values of the of the measured biologic impedance at each of the plurality of surface sensors.

5. The method of claim 3, wherein the first axis and the second axis are generally orthogonal to each other.

6. The method of claim 3, wherein
the step of driving further comprises driving a third dipole along a third axis across the patient's body;
the step of calculating further comprises calculating means of the absolute values of the measured biologic impedance as a function of time at the at least one surface sensor with respect to each of the first dipole, the second dipole, and the third dipole separately as Pm(t,i);
the step of saving further comprises saving an initial calculated mean of the absolute values of the measured biologic impedance for each of the first dipole, the second dipole, and the third dipole separately as Pa(i); and
the step of multiplying further comprises multiplying an impedance measurement at the measurement electrode with respect to each of the first dipole, the second dipole, and the third dipole by the respective ratio of Pa(i)/Pm(t,i).

7. The method of claim 6, wherein
the at least one surface sensor comprises a plurality of surface sensors;
the step of calculating further comprises calculating the mean of the absolute values of the measured biologic impedance as a function of time at each of the plurality of surface sensors; and
the step of saving further comprises saving the initial calculated mean of the absolute values of the of the measured biologic impedance at each of the plurality of surface sensors.

8. The method of claim 6, wherein the first axis, the second axis, and the third axis are generally orthogonal to each other.

9. The method of claim 1, wherein the step of driving comprises electrically exciting a pair of surface electrodes on the patient's body to act as a source and a drain, respectively.

10. A method for determining a position of at least one measurement electrode within a patient's body, the method comprising
positioning a plurality of surface electrodes on a surface of the patient's body;
electrically driving a first pair of the plurality of surface electrodes on the patient's body to act as a source and a drain;
sensing at least one impedance value at at least one of the plurality of surface electrodes that is not one of the driven pair of surface electrodes;
measuring an impedance between the at least one measurement electrode and a reference electrode;
repeating the steps of driving, sensing, and measuring for a second pair of the surface electrodes and a third pair of the surface electrodes;
scaling the impedance sensed at at least one of the surface electrodes for each step of sensing and measuring by
calculating the mean of the absolute value of the at least one sensed impedance continuously as a function of time Pm(t);
saving an initial calculated mean of the absolute value of the at least one sensed impedance as Pa; and
multiplying the impedance measurement between the at least one measurement electrode and the reference electrode by the ratio of Pa/Pm(t); and
identifying the position of the at least one measurement electrode within the patient's body as a function of the scaled impedance.

11. The method of claim 10, wherein
the step of calculating further comprises calculating means of the absolute values of the measured biologic impedance as a function of time at the at least one of the plurality of surface electrodes that is not one of the driven pair of surface electrodes with respect to each of the first pair of the surface electrodes, the second pair of the surface electrodes, and the third pair of the surface electrodes separately as Pm(t,i);

the step of saving further comprises saving an initial calculated mean of the absolute values of the measured biologic impedance for each of separately as Pa(i); and the step of multiplying further comprises multiplying an impedance measurement at the measurement electrode with respect to each of the first pair of the surface electrodes, the second pair of the surface electrodes, and the third pair of the surface electrodes by the respective ratio of Pa(i)/Pm(t,i).

12. The method of claim 10, wherein respective axes between each of the first, second, and third pairs of surface electrodes are generally orthogonal to each other.

13. The method of claim 10, wherein the step of sensing further comprises sensing the impedance value at each of the plurality of electrodes that is not one of the driven pair of electrodes.

14. The method of claim 10, wherein the step of sensing further comprises sensing the impedance value at a subset of the plurality of electrodes that does not include one of the driven pair of electrodes.

15. The method of claim 10, wherein the reference electrode is within the patient's body.

16. The method of claim 10, wherein the reference electrode is on the surface of the patient's body.

17. The method of claim 10, wherein the step of positioning further comprises categorizing the plurality of electrodes into two or three pairs of electrodes orienting each pair of electrodes such that an axis between electrodes in each pair of electrodes is generally orthogonal to axes between electrodes in the other pairs of electrodes.

\* \* \* \* \*

UNITED STATES PATENT AND TRADEMARK OFFICE
CERTIFICATE OF CORRECTION

PATENT NO. : 7,885,707 B2  
APPLICATION NO. : 11/227580  
DATED : February 8, 2011  
INVENTOR(S) : John A. Hauck It is certified that error appears in the above-identified patent and that said Letters Patent is hereby corrected as shown below:

In The Claims

Column 7, claim 2, line 38, kindly delete "of the of the" and replace with --of the--.

Column 7, claim 4, line 65, kindly delete "of the of the" and replace with --of the--.

Column 8, claim 7, line 28, kindly delete "of the of the" and replace with --of the--.

Column 8, claim 10, line 44, kindly delete "at at" and replace with --at--.

Column 8, claim 10, line 52, kindly delete "at at" and replace with --at--.

Signed and Sealed this  
Twenty-ninth Day of March, 2016

Michelle K. Lee  
*Director of the United States Patent and Trademark Office*